United States Patent [19]

Favaloro

[11] 4,417,589
[45] Nov. 29, 1983

[54] RESPIRATION MONITOR FOR MAMMALS

[76] Inventor: William E. Favaloro, 2029 Fern St., New Orleans, La. 70118

[21] Appl. No.: 275,038

[22] Filed: Jun. 18, 1981

[51] Int. Cl.³ .............................................. A61B 5/08
[52] U.S. Cl. .................................................. 128/716
[58] Field of Search ........... 128/716, 725, 727, 204.23, 128/726, 724

[56] References Cited

U.S. PATENT DOCUMENTS

| 793,177 | 6/1905 | Cady | 128/727 |
|---|---|---|---|
| 3,347,222 | 10/1967 | Kohrer | 128/716 |
| 3,357,428 | 12/1967 | Carlson | 128/204.23 |
| 3,817,238 | 6/1974 | Matson | 128/716 |
| 3,898,987 | 8/1975 | Elam | 128/716 |
| 4,158,360 | 6/1979 | Adams | 128/725 |
| 4,241,739 | 12/1980 | Elson | 128/725 |

Primary Examiner—Kyle L. Howell
Assistant Examiner—Mitchell J. Shein

[57] ABSTRACT

A monitoring system for the breathing of mammals is comprised of a gas monitor having a gas-flow detector tube in which positioning of a ball triggers a signal alerting appropriate personnel when the mammal's breathing has stopped.

10 Claims, 3 Drawing Figures

RESPIRATION MONITOR FOR MAMMALS

This invention relates to the monitoring of breathing of mammals during periods in which close intensive care is impossible or impractical.

In veterinary hospitals, and in non-clinical or semi-clinical situations for both humans and animals, it is often desirable to monitor respiration without the elaborate and expensive close intensive care facilities which can be provided in most modern medical hospitals.

For example, veterinary hospitals and veterinary clinics have no practical means for monitoring an animal's critical respiration during and after surgery. It is neither practical or economically feasible to have a veterinarian or assistant constantly visually monitoring respiration.

Infant children and elderly not uncommonly undergo prolonged periods of high life vulnerability in which hospitalization may be impractical but in which observation or monitoring is desirable and help should be readily available.

Knowing at an early stage when a breathing problem is occurring allows as much time as possible for corrective action to be taken to prevent death. Every second of reaction time is critical during period of shock, weakness or vulnerability since the condition of the mammal can change drastically in a short period of time.

It is, therefore, an objective of this invention to provide a reliable monitoring system to monitor respiration of mammals with an alarm to signal cessation of breathing or excessive time lapse between each breath.

SUMMARY OF THE INVENTION

Briefly, the invention is a monitoring system comprising at least one and preferably two gas-flow detector tubes in conjunction with an endotracheal tube assembly, at least one of an intake conduit and an exhaust conduit. The detector tubes each contain a gas-flow indicator ball with a means for stopping the ball at a given position when there is no gas flow. Light ignition and detection means at the stopping position trigger a signal when the ball is moved from the no-flow stop position. The signal may cause the discontinuance of a continuing sound or light, or the starting of a sound or light.

In a preferred embodiment, both intake and exhaust conduits are used and the detector tube or tubes are connected on one end with the endotracheal tube (and, if the system is used in conjunction with an oxygen machine,) on the other end with the (oxygen) machine.

In the detailed description, reference will be made to the drawing in which FIG. 1 shows schematically one aspect of this invention which is the monitoring system in conjunction with an oxygen machine; FIG. 2 shows schematically a monitoring system not in conjunction with the breathing machine; and FIG. 3 shows in detail a dual tube gas flow monitor such as depicted in FIGS. 1 and 2.

DETAILED DESCRIPTION OF THE INVENTION

The terms "endotracheal tube " or "endotracheal assembly" as used herein refers to any means for connecting the respiratory system of a mammal with a gas supply and/or gas exhaust conduit and monitoring system, and specifically includes an endotracheal tube, gas mask, or gas enclosure.

Figure 3:
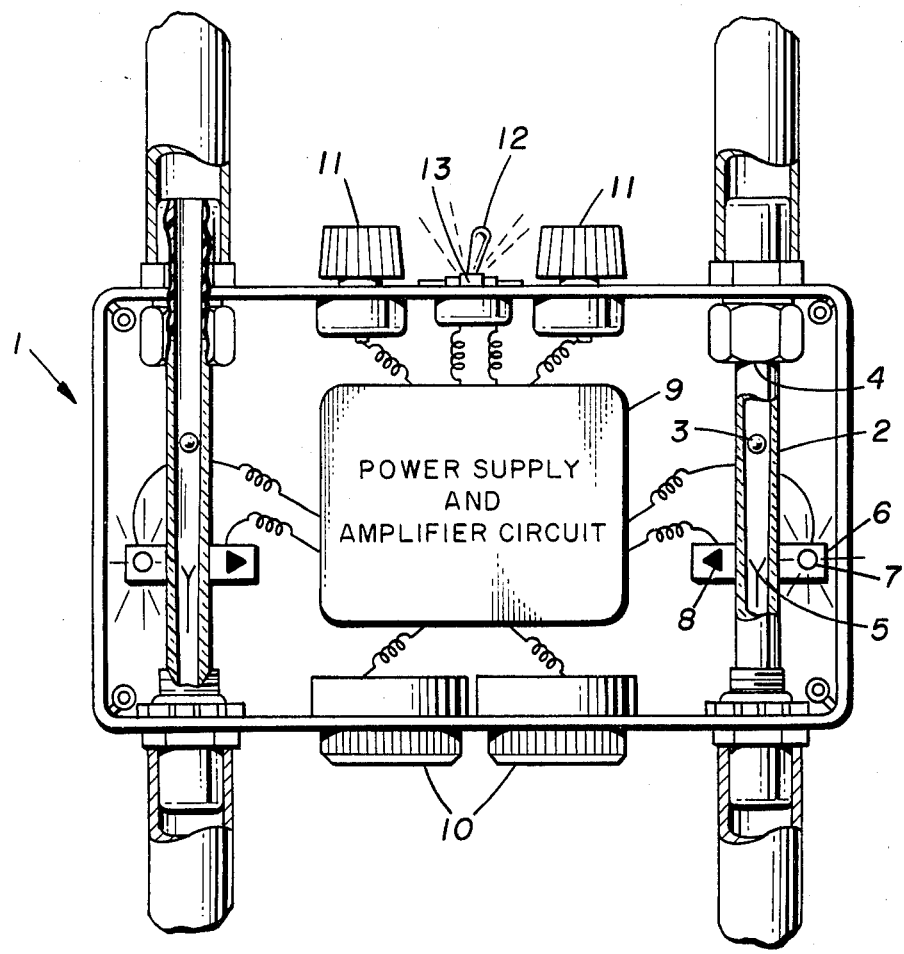

Referring in detail to FIG. 3, box 1 has two flow detector tubes (2). Each flow detector tube is designed with a tapered hole, the smaller diameter being at the bottom and the larger at the top. The flow detector tube is tapered to provide sensitivity to gas flow; to allow freedom of gas flow without any gas stoppage; and gas flow detection with minimum flow restriction. There is a ball (3) inside the flow detector tube which rises higher as the gas flow increases. There is a top stop (4) and a bottom stop (5) to keep the ball inside the flow detector tube.

Block (6) is mounted on the flow detector tube at a level which is the same as the ball when the ball is sitting on the bottom stop, at which time there is no gas flow. The block contains a light emitting diode (7) and a photodetector (8).

When the ball is on the lower stop, at which time there is no gas flow, light from the light emitting diode is unable to shine through the flow detector tube and flow ball and be detected by the photo detector. When gas flows and the ball rises off the bottom stop, light from the light emitting diode is detected by the photo detector.

The photo detector is connected to an amplifier circuit (9) which in turn is capable of amplifying the small signal received from the photo detector and sounding the buzzer (10).

The photo detector, light emittiong diode, and buzzer circuit are operated from a DC power source that can be either batteries or a rectifier power source.

There is a volume control (11) in the amplifying circuit to control the amplitude of sound coming from the buzzer. There is also a power supply "on-off" switch (12) and a power "on" indicating light (13).

Figure 1:
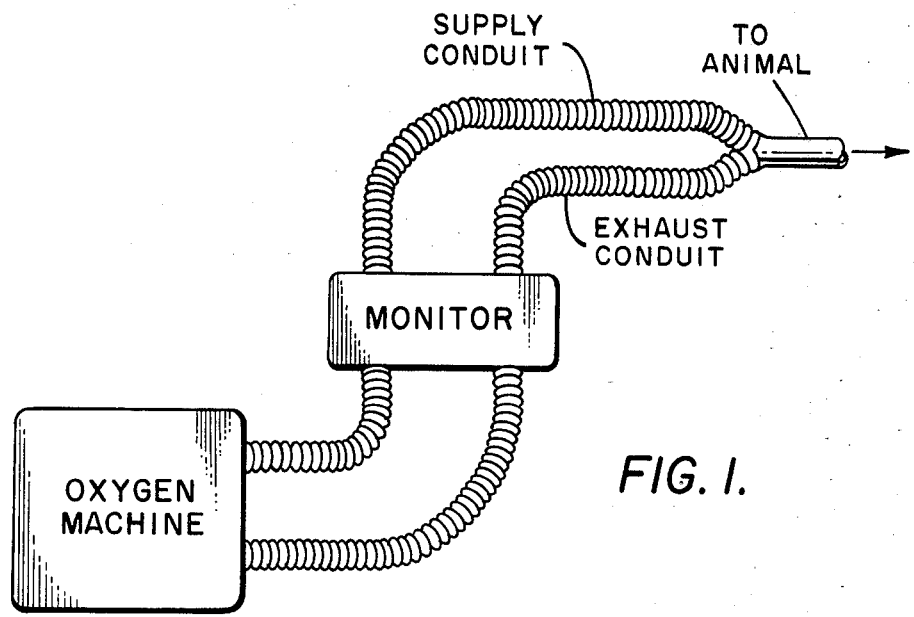
Figure 2:
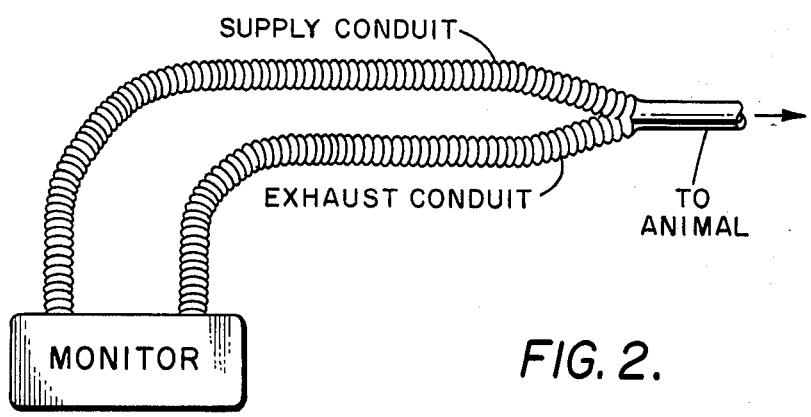

In operation, one tube will operate each from the supply and exhaust conduit (see FIGS. 1 and 2). Each flow indicator tube is wired so that when the flow indicator ball is in the no-flow stop position, no light will be detected by the photo detector (8), and the signal to buzzers (10) will cease. If the mammal stops breathing entirely, there will be no activity in either of the flow detector tubes, and neither of the buzzers will operate.

I claim:

1. A system for assisting and monitoring the breathing of mammals comprising in combination:
(1) a breathing machine having means for supplying a breathing gas and means for exhausting an oxygen-depleted breathing gas, said supplying and exhausting means each comprising at least one gas conduit for an intermittent essentially unidirectional main stream conduit gas flow; having in conjunction with at least one of the gas conduits a gas flow monitor comprising a tapered in line generally vertically disposed double ended through-flow gas flow indicator tube having an entry end and an exit end and having a taper between the entry end and the exit end from a lower smaller diameter to an upper larger diameter, connected on both ends with the gas conduit and containing a gas flow-indicator ball having a diameter generally less than the diameter of at least a portion of the length of the tube disposed to rest directly against and rise with the main stream conduit gas flow, means for stopping the ball at a given bottom position when there is no gas flow, light emission and detection means at said bottom no-flow position whereby a light is directed through the tube and its rays are detected when not obstructed by the ball, and monitor signal means responsive to the light detection means whereby a signal is provided when the ball is moved from the bottom no-flow position, and an alarm responsive to said signal.

2. A system for assisting and monitoring the breathing of mammals comprising in combination:
(1) a breathing machine having means for supplying a breathing gas, means for exhausting an oxygen-depleted breathing gas, the supply means including a supply conduit for an intermittent essentially unidirectional main supply gas stream and the exhaust means including an exhaust conduit for an intermittent essentially unidirectional main exhaust gas stream and
(2) a breathing monitor comprising
  (a) a gas exhaust flow monitor comprising tapered in line generally vertically disposed double ended through flow gas flow indicator tube having an entry end and an exit end and having a taper between the entry end and the exit end from a lower smaller diameter to an upper larger diameter connected on one side of the tube with the exhaust conduit and on the other side of the tube with an endotracheal tube and containing a gas flow indicator ball having a diameter generally less than the diameter of at least a portion of the length of the tube disposed to rest directly against and rise with the main exhaust gas stream flow, the indicator tube having means for stopping the ball at a given bottom position when there is no exhaust gas flow; light emission and detection means at the said given bottom no-flow position whereby a light is directed through the tube and its rays are detected when not obstructed by the ball, and monitor signal means responsive to the light detection means whereby a signal is provided when the ball is moved from the no-flow position at the said ball stop means and an alarm responsive to said signal; and
  (b) a gas supply flow monitor comprising a tapered in-line generally vertically disposed gas flow indicator tube having an entry end and an exit end and having a taper between the entry end and the exit end from a lower smaller diameter to an upper larger diameter connected on one side of the tube with the supply conduit and on the other side of the tube with an endotracheal tube and containing a gas flow indicator ball having a diameter slightly less than the diameter of at least a portion of the length of the tube disposed to rest directly and rise with the main supply gas stream; the indicator tube having means for stopping the ball at a given bottom position when there is no supply gas flow; light emission and detection means at the said given bottom position whereby a light is directed through the tube and its rays are detected when not obstructed by the ball; and monitor signal means responsive to the light detection means whereby a signal is provided when the ball is moved from the no-flow bottom position at the said ball stop means, and an alarm responsive to said signal.

3. The system of claim 2 wherein the gas flow indicator tubes are tapered.

4. The system of claim 2 wherein the alarm means provided when the ball comes to rest includes means for discontinuing an otherwise continuous sound.

5. The system of claim 2 wherein the alarm means includes means for discontinuing an otherwise continuous light and sound.

6. A monitoring system for the breathing of mammals comprising in combination:
an endotracheal assembly comprising at least one gas conduit, a gas flow indicator tube connected on one side of the tube with an exhaust/supply conduit and on the other side of the tube with the endotracheal assembly and containing a gas flow-indicator ball, having a diameter generally less than the diameter of the tube, the indicator ball having means for stopping the ball at a given position when there is no exhaust-supply gas flow; light emission and detection means at the said given position whereby a light is directed when not obstructed by the ball, and monitor signal means responsive to the light detection means whereby a signal is provided when the ball is not in the no-flow position at the said ball stop means, and an alarm responsive to said signal.

7. A monitoring system for the breathing of mammals comprising in combination an endotracheal tube assembly, an intake conduit, an exhaust conduit; and at least one of
(a) a gas exhaust monitor comprising a gas-flow indicator tube connected on one side of the tube with the exhaust conduit and on the other side of the tube with the endotracheal assembly and containing a gas flow-indicator ball, having a diameter generally less than the diameter of the tube, the indicator tube having means for stopping the ball at a given position when there is no exhaust gas flow; light emission and detection means at the said given position whereby a light is directed through the tube and its rays are detected when not obstructed by the ball, and monitor signal means responsive to the light detection means whereby a signal is provided when the ball is moved from the no-flow position at the said ball stop means, and an alarm responsive to said signal,
(b) a gas supply monitor comprising a gas flow indicator tube connected on one side of the tube with the supply conduit and on the other side of the tube with the endotracheal assembly and containing a gas flow indicator ball having a diameter slightly less than the diameter of the lower end of the taper indicator tube; the indicator tube having means for stopping the ball at a given position when there is no supply gas flow; light emission and detection means at the said given position whereby a light is directed through the tube and its rays are detected when not obstructed by the ball, and monitor signals means responsive to the light detection means whereby a signal is provided when the ball is moved from the no-flow position at the said ball stop means, and an alarm responsive to said signal.

8. The system of claim 6 wherein the gas-flow indicator tube is tapered.

9. The system of claim 6 wherein the alarm means provided when the ball comes to rest includes means for discontinuing an otherwise continuous sound.

10. The system of claim 6 wherein the alarm means includes means for discontinuing an otherwise continuous light and sound.

* * * * *